US00PP17326P3

(12) United States Plant Patent
Houbraken

(10) Patent No.: US PP17,326 P3
(45) Date of Patent: Jan. 2, 2007

(54) ***BIDENS FERULIFOLIA* PLANT NAMED 'BIDCOMTIS'**

(50) Latin Name: *Bidens ferulifolia*
Varietal Denomination: Bidcomtis

(75) Inventor: Annemarie Houbraken, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 6 days.

(21) Appl. No.: 10/899,777

(22) Filed: Jul. 27, 2004

(65) Prior Publication Data

US 2006/0026727 P1 Feb. 2, 2006

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

GTITM UPOV ROM Citation for 'Bidcomtis' as per QZ PBR 030450, Jun. 15, 2003.*

* cited by examiner

*Primary Examiner*—Kent Bell
*Assistant Examiner*—Louanne Krawczewicz Myers
(74) *Attorney, Agent, or Firm*—Bruce Vrana

(57) ABSTRACT

A distinct cultivar of *Bidens* plant named 'Bidcomtis' which is particularly distinguished by its very compact plant habit, short internodes, and golden yellow flowers. The new cultivar can perfectly be used in 10–12 cm pots and grown without growth regulators.

1 Drawing Sheet

Latin name of the genus and species of the plant claimed: *Bidens ferulifolia.*
Varietal denomination: 'Bidcomtis'.

BACKGROUND OF THE NEW PLANT

The present invention relates to a new distinct cultivar of *Bidens,* botanically known as *Bidens ferulifolia,* native to South USA and Mexico.

The new cultivar is propagated by cuttings resulting from a seedling from *Bidens ferulifolia* cv. 'Bidtis 1' (U.S. Plant Pat. No. 12,280). Seed of 'Bidtis 1,' resulting from open pollination, was harvested in 1999 and a new variety 'Bidcomtis' was selected in 2000 as one of the plants of this population. This new plant is an annual. The new cultivar is a product of a planned breeding program conducted by the inventor in Enkhuizen, The Netherlands. The objective of the breeding program was to develop a compact *Bidens* variety. 'Bidcomtis' was asexually reproduced by cuttings for 3 years now and trialed under different conditions in Europe on Syngenta trial ground properties. It has been found to retain its distinctiveness characteristics through successive propagation, and its novelty appears to be firmly fixed. The new variety reproduces true to type in successive generations of asexual reproduction.

DESCRIPTION OF THE DRAWING

This new *Bidens* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Bidens* plant. The data which defines these characteristics were collected from asexual reproductions carried out in Enkhuizen, Netherlands. The plant history was taken on 20 weeks old plants, grown in window boxes in Enkhuizen, The Netherlands with day temperatures ranging from 16 and 30 degrees Celsius, and night temperatures ranging from 10 to 16 degrees Celsius.

Color references are primarily to the RHS Color Chart of The Royal Horticultural Society of London.

TABLE 1

DIFFERENCES BETWEEN THE NEW CULTIVAR 'BIDCOMTIS' AND 'BIDTIS 1'

| | 'Bidcomtis' | 'Bidtis 1' |
|---|---|---|
| Plant Height | 28–30 cm | 40–50 cm |
| Plant Width | 60 cm | 100–120 cm |
| Seed set | Present | Absent |
| Internode length | 3–4 cm | 8–10 cm |

The plant:

*Classification.*—Botanical: *Bidens ferulifolia* cv. 'Bidcomtis'.

Parentage:

*Female parent.*—*Bidens ferulifolia* cv. 'Bidtis 1' (U.S. Plant Pat. No. 12,280); Breeders code of the new plant 'Bidcomtis' is B 72-4.

*Male parent.*—Unnamed selection of *Bidens ferulifolia* (unpatented).

Propagation:

*Type cuttings.*—Terminal cuttings.

*Time to initiated roots.*—10–12 days at air temperature of 21 degrees C.

*Time to develop roots.*—14–18 days at air temperature of 17 degrees C.

Plant description:

*Growth habit.*—Ball shaped, with trailing branches at the bottom of the plant.

*Plant height.*—28–30 cm.

*Vigor.*—Less vigorous than *Bidens ferulifolia* cv. 'Bidtis 1' and 'Peter's Goldteppich' (U.S. Plant Pat. No. 12,880).

*Spreading area of plant.*—60 cm.

*Strength.*—Resistant to hot and cold weather.

*Branching character.*—Freely branching and lateral branching at every node.

*Number of branches per plant.*—8 branches/plant.

*Crop time.*—12 weeks.

The stem:

*Diameter.*—4 mm.

*Shape.*—Cylindrical.

*Length of the plant stem.*—Up to 30 cm.

*Length of the lateral branch.*—Up to 30 cm.

*Anthocyanin pigmentation.*—Present, can get as dark as RHS 79B in old stems.

*Length of internode.*—3–4 cm depending on light conditions.

*Pubescence.*—Absent.

*Color.*—Young stem: 152A. Older stem: Between 59A and N79B with anthocyan pigmentation.

The foliage:

*Arrangement.*—Opposite, but alternate on flower stems.

*Shape of leaf.*—2-pinnate fern-like leaves.

*Leaf apex.*—Apiculate.

*Leaf base.*—Acute.

*Leaf margin.*—Laciniate.

*Texture.*—Smooth young leaves.

*Leaf length.*—3–4 cm.

*Leaf width.*—2–2.5 cm.

*Depth of incision.*—Fully incised.

*Color.*—Upper side: Young leaf 143A. Old leaf 146A. Lower side: Young leaf 144A. Old leaf 146C.

*Pubescence.*—Absent.

*Petiole.*—Length: 0.5–1.0 cm. Color: 152A. Diameter: 1 mm.

*Venation.*—Shape: Pinnate. Color: 143B, upper and lower surface.

The bud:

*Peduncle.*—Length: 3–4 cm. Diameter: 1 mm. Angle: 45° at base of peduncle; bending more towards main stem at the end. Strength: Flexible. Color: Green, RHS 143 A, occasionally some anthocyanin pigmentation; RHS 79B.

*Size of the bud.*—Length: 0.5–0.8 cm. Diameter: 0.3–0.5 cm.

*Shape.*—Oblong.

*Color.*—14A.

Inflorescence:

*Flowering season.*—Continuous and free flowering throughout spring and summer; less floriferous during the fall.

*Diameter of disc.*—2.8–3.2 cm.

*Depth of disc.*—8 mm.

*Form.*—Capitulum with 1 series of ray florets and more series of disc florets.

*Overlapping of ray florets.*—Separate ray florets, but little overlap in flower head.

*Receptacle.*—Shape: Brush-shape. Height: 4 mm. Color: 145A.

*Fragrance.*—Weak.

*Number of inflorescences per plant.*—±100 inflorescences per plant depending on growth conditions and age of plant.

*Lastingness of inflorescences on plant.*—7 days.

Ray florets:

*No. of ray florets per inflorescence.*—5.

*Size.*—Length: 13–17 mm. Width: 8–10 mm.

*Ray floret.*—Shape: Ovate. Apex: Tri-dentate. Base: Obtuse. Margin: Entire. Texture: Smooth.

*Color of upper and lower side.*—More bright and intense golden yellow than 9A.

Disc florets:

*No. of disc florets per inflorescence.*—±70 disc florets/inflorescence.

*Size.*—Length: 4–6 mm. Width: 1 mm.

*Disc of floret.*—Shape: Tubular, elongated. Apex: Five-pointed. Base: Fused. Margin: Entire. Texture: Smooth.

*Color of upper and lower side.*—13A.

Phyllary:

*Number of phyllaries.*—7, occassionally 6 or 8 green ones (RHS 137C) at the lower part of the receptacle and 6–8 yellow ones (RHS 9A) near the ray florets.

*Size.*—Length: 4 mm. Width: 1 mm.

*Phyllary.*—Shape: Elongated elliptic. Apex: Acute. Base: Truncate. Margin: Entire. Texture: Very lightly pubescent.

Androecium:

*Location.*—Present on disc florets only.

*Anther color.*—200A.

*Anther size.*—1.3 mm long.

*Stamen number.*—5.

*Pollen color.*—17A.

*Amount of pollen.*—Few.

Gynoecium:

*Location.*—Present on ray and disc florets.

*Pistil number.*—±70 pistils/inflorescence.

*Pistil length.*—6.5 mm.

*Style length.*—3 mm.

*Ovary.*—Number: One per pistil. Size: 0.3 mm diameter, 1.3 mm long.

*Ovary color.*—149C.

*Style color.*—15A.

*Stigma shape.*—Bifurcate.

*Stigma color.*—15A.

Seed:

*Production.*—Yes.

*Size.*—Length: 0.5–0.7 cm. Diameter: 0.8 mm.

*Color.*—202A.

*Shape.*—2 rigid awns with minute reflexed points on the achene.

Disease/pest resistance and tolerance for weather conditions: Good tolerance to heat. No specific susceptibility for pests or diseases has been observed.

What is claimed is:

1. A new and distinct variety of *Bidens* plant, substantially as herein illustrated and described, characterized particularly as to novelty by its very compact plant habit with short internodes and bright golden yellow flowers.

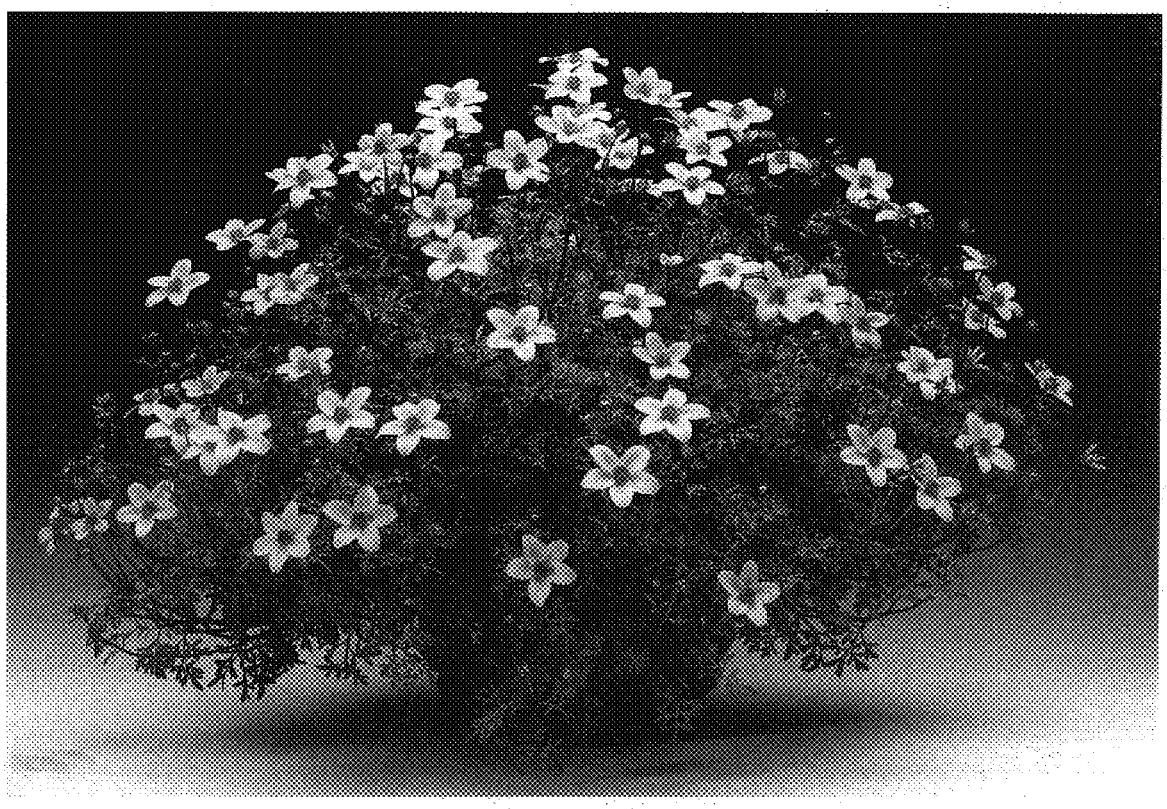

* * * * *